United States Patent
Sano et al.

(10) Patent No.: US 7,371,305 B2
(45) Date of Patent: May 13, 2008

(54) TUBE CONNECTING APPARATUS AND TUBE CONNECTING METHOD

(75) Inventors: Hiroaki Sano, Nakakoma-gun (JP);
Masaru Nagashimada, Nakakoma-gun (JP); Shinji Ishida, Isehara (JP);
Satoshi Yamanushi, Nirasaki (JP);
Hideya Fujihara, Nirasaki (JP);
Osamu Sumiya, Kofu (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 424 days.

(21) Appl. No.: 10/525,979

(22) PCT Filed: Aug. 29, 2003

(86) PCT No.: PCT/JP03/11044
§ 371 (c)(1),
(2), (4) Date: Feb. 28, 2005

(87) PCT Pub. No.: WO2004/022317
PCT Pub. Date: Mar. 18, 2004

(65) Prior Publication Data
US 2006/0054275 A1    Mar. 16, 2006

(30) Foreign Application Priority Data
Aug. 30, 2002 (JP) .............................. 2002-252457

(51) Int. Cl.
B32B 37/00 (2006.01)
B29C 65/00 (2006.01)

(52) U.S. Cl. ................ 156/296; 156/304.1; 156/304.2; 156/538; 156/539; 156/556

(58) Field of Classification Search ............. 152/304.1, 152/304.2, 304.6, 296, 538, 539, 556
See application file for complete search history.

(56) References Cited

FOREIGN PATENT DOCUMENTS

| EP | 0 044 204 A2 | 1/1982 |
|---|---|---|
| EP | 0 507 321 A1 | 10/1992 |
| EP | 0 515 811 A2 | 12/1992 |
| EP | 0 778 123 A2 | 6/1997 |
| JP | 61-30582 | 7/1986 |
| JP | 4-308731 | 10/1992 |
| JP | 6-91010 | 4/1994 |
| JP | 07329182 | * 12/1995 |
| JP | 9-154920 | 6/1997 |

* cited by examiner

Primary Examiner—Justin Fischer
(74) Attorney, Agent, or Firm—Buchanan Ingersoll & Rooney PC

(57) ABSTRACT

A tube-joining apparatus capable of stably and reliably joining tubes where liquid is contained and sealed. In a tube joining apparatus, a first clamp (6) and second clamp (7) for pressing and holding tubes (8, 9) are arranged in a contact state. When a second moving mechanism is driven to separate the second clamp (7) from the first clamp (6), the first clamp (6) is slid on the tubes by a shaft (121) supporting the first clamp (6) in a vertically movable manner and is moved from a first position (P1) to a second position (P2). The tubes are squeezed with a pressing force being gradually increased while the tubes are slid between slants (67, 77) of an engagement portion (68) and second engagement portion (78). Residual liquid in the tubes is removed from inside the tubes by the squeezing operation of the first clamp 6. The tubes from which the residual liquid is removed are cut by a cutting plate (41), the tubes are moved by first and second moving mechanisms, and then the tubes are joined.

11 Claims, 10 Drawing Sheets

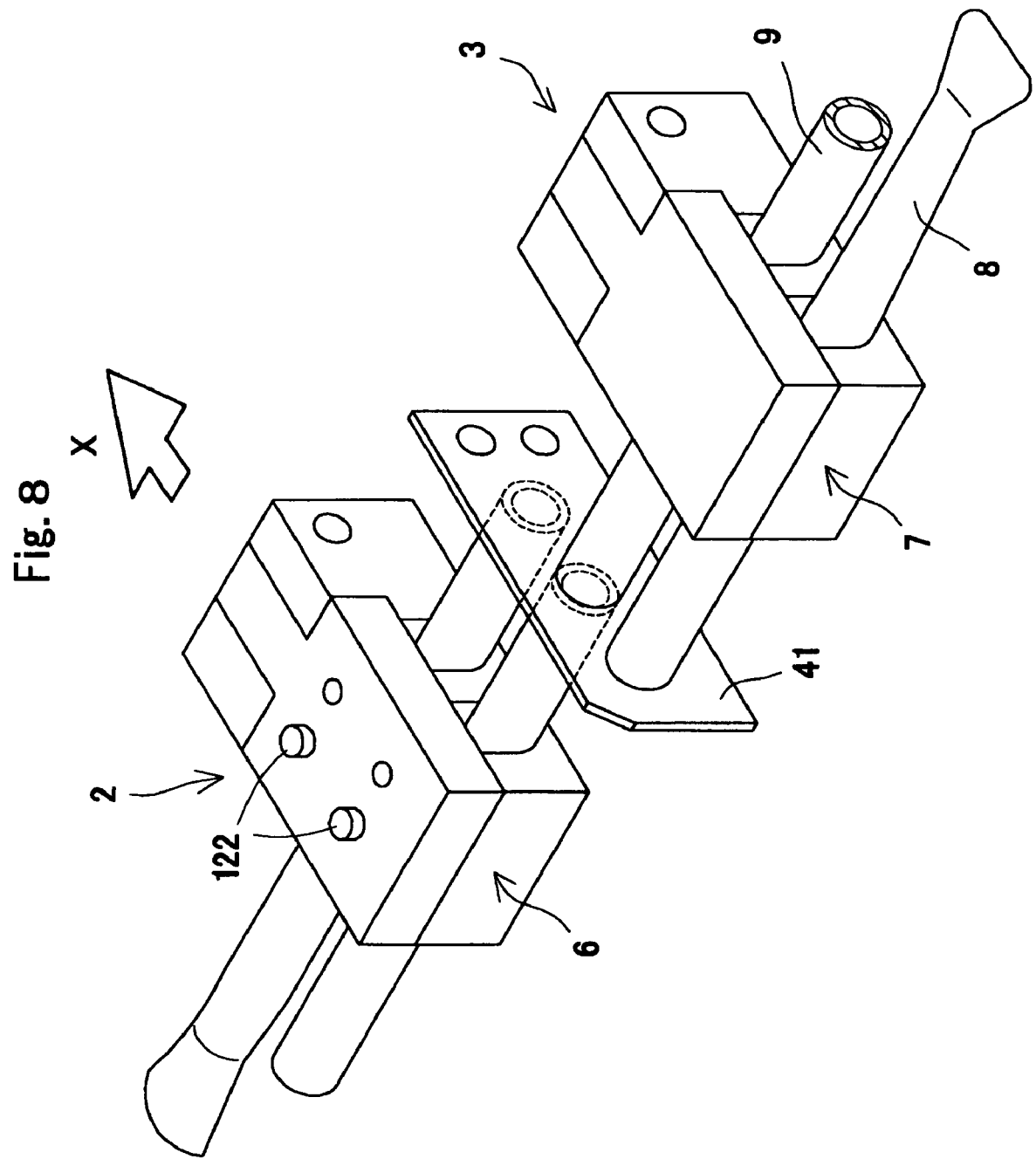

TUBE CONNECTING APPARATUS AND TUBE CONNECTING METHOD

BACKGROUND OF THE INVENTION

1. Field of the Invention

The present invention relates to a tube connecting apparatus and a tube connecting method that cuts and then connects flexible tubes, and in particular relates to a tube connecting apparatus and a tube connecting method that melts at least two flexible tubes by heat and then connects the tubes under a sterilized condition.

2. Description of Related Art

Conventionally, in a case that tube connecting between a blood-collecting bag and a blood-component bag in a blood transfusion system, exchanging between a dialytic-fluid bag and a waste-fluid bag in continuous ambulatory peritoneal dialysis (CAPD) or the like is carried out, it is necessary to connect (join) tubes under a sterilized condition. An example of such an apparatus for connecting tubes under a sterilized condition is disclosed in JPB 61-30582. This tube connecting apparatus is equipped with a pair of holders (blocks) capable of holding two tubes to be connected in parallel and a cutting plate (plate-shaped heater element) capable of moving across the tubes which are placed between both of the holders. In the tube connecting apparatus, the cutting plate is heated and moved to melt and cut the tubes in a state that the two tubes are held in parallel and in an opposite direction in grooves which are formed at the holders, then one of the holders is moved in a diameter direction (row direction) of the tubes to coincide cut ends of the tubes to be connected each other, and the cutting plate is extracted by moving it to an evacuated position to fuse (melt and connect) both of the tubes.

Further, a tube connecting apparatus having a first clamp and a second clamp which hold two tubes in a parallel state, which employs the same tube connecting method as the above apparatus in order to improve reliability of tube connecting, and which is equipped with a first clamp movement mechanism that moves the first clamp in parallel to the second clamp, namely, that carries out merely forward or backward movement for advancing or retracting the first clamp, and a second clamp movement mechanism that moves the second clamp merely in a direction that the second clamp approaches/separates to/from the first clamp, is disclosed in JPA 6-91010.

Furthermore, an apparatus, which employs the same principle of heating, melting and then connecting tubes each other under a sterilized condition by utilizing a cutting plate, yet which connects the tubes in a state that liquid in the tubes is kept contained without leaking the liquid even in a case that the liquid remains inside the tubes before the tubes are cut, is disclosed. For example, JPA 4-308731 discloses a technique that two tubes (a first tube, a second tube) are held on the same rotation locus respectively according to a pair of tube holders allowed to rotate relatively, after the two tubes are cut between the holders by a heated cutting plate, the tube holders are rotated such that a cut end face of one end side of the first tube aligns (corresponds to) a cut end face of another side of the second tube, and the cutting plate is evacuated to fuse both of the tubes. Moreover, a tube connecting apparatus which is capable of not only connecting tubes in a state that liquid inside the tubes is kept contained and sealed without leaking the liquid but which can realize downsizing of the apparatus and of parts for the apparatus due to a small moving amount of the tubes at the time of connecting the tubes, is also disclosed. For example, JPA 9-154920 discloses a technique that two tubes to be connected are accommodated and held in two tube-holding assembly (a first tube-holding assembly, a second tube-holding assembly) in a contacted (piled) state with each other, after the two tubes are cut by a heated cutting plate, the second tube-holding assembly is rotated by 180 degrees relatively to the first tube-holding assembly such that cut end faces of the tubes are replaced with each other for alignment, and the cutting plate is evacuated to fuse both of the tubes.

However, in the conventional tube connecting apparatuses, even in any embodiment of the apparatuses in which the two tubes are arranged in parallel in a horizontal or vertical direction in a separated or contacted state, if liquid inside the tubes includes protein such as blood or the like, residual liquid inside the tubes between the two tube-holding assemblies (holders) remains at the end faces of the tubes to be connected when the tubes are cut by the cutting plate. For this reason, there is a problem in that connecting strength between the tubes is remarkably weakened. Namely, in the conventional apparatuses, in a case that liquid is contained and sealed in either one of the tubes, since the tube end face of one side thereof is moved in a state of contacting the cutting plate at the time of moving the tube-holding assembly so as to face the end portions of the tubes to be connected each other via the cutting plate and the residual liquid in the tubes is excluded or removed to some degree at this time, it is possible to connect the tubes each other although connecting strength thereof is lowered. However, they could not connect two tubes each other stably in a case that both of the two tubes contain and seal liquid such as blood or the like.

SUMMARY OF THE INVENTION

In view of the above circumstances, an object of the present invention is to provide a tube connecting apparatus and a tube connecting method capable of connecting tubes in which liquid is contained and sealed each other stably and reliably.

In order to achieve the above object, a first aspect of the present invention is directed to a tube connecting apparatus having a first holding assembly and a second holding assembly which hold at least two flexible tubes approximately in a parallel state, comprising: a first pressing unit which is provided at the first holding assembly and which presses the tubes to a flat state; a second pressing unit which is provided at the second holding assembly and which presses the tubes to a flat state and which is allowed to be located so as to contact the first pressing unit; a cutting unit which cuts the tubes between the first and second pressing units; a first movement unit which moves at least one of the first and second holding assemblies to change relatively positions of the tubes cut by the cutting unit such that end portions to be connected face each other; and a second movement unit which moves at least one of the first and second holding assemblies in a direction that the first pressing unit and the second pressing unit separate and a direction that the end portions to be connected of the tubes cut by the cutting unit contact closely each other.

In the first aspect, the second pressing unit is located so as to contact the first pressing unit, at least two flexible tubes held approximately in a parallel state by the first holding assembly and the second holding assembly are pressed to a flat state by the first and second pressing units, then at least one of the first and second holding assemblies is driven to move in a direction that the first pressing unit and the second pressing unit separate by the second movement unit such that the first pressing unit presses the tubes to exclude residual liquid inside the tubes between the second pressing unit and the first pressing unit. The tubes are cut by the cutting unit at a position between the separated first and second pressing units at which the residual liquid is excluded, the at least one of the first and second holding assemblies is driven to move to change relatively positions of the tubes cut by the cutting unit such that end portions to be connected face each other by the first movement unit, and the at least one of the first and second holding assemblies is driven to move in a direction that the end portions to be connected of the tubes contact closely each other by the second movement unit, then the tubes are connected with each other. According to this aspect, since the first pressing unit presses the tubes to exclude the residual liquid inside the tubes, even if liquid is contained and sealed in the tubes, when the tubes are cut by the cutting unit and the at least one of the first and the second holding assemblies is driven to move by the first and second movement units to connect the tubes, the tubes are connected with each other without being influenced by the liquid contained and sealed in the tubes.

In the first aspect, the tube connecting apparatus may further comprise a supporting member which supports at least one of the first and second pressing units such that a pressing amount of the at least one of the first and second pressing units to the tubes changes. In this case, it is preferable to further comprise a position regulating member which regulates at a predetermined position the at least one of the first and second pressing units supported by the supporting member. Further, the first pressing unit may have a first engagement portion and the second pressing unit may have a second engagement portion, and when the at least one of the first and second holding assemblies is driven to move in a direction that the holding assemblies separate from each other by the second movement unit, the supporting member may gradually change the pressing amount of the at least one of the first and second pressing units to the tubes in accordance with a moving amount of the supporting member. At this time, it is preferable that the first engagement portion and the second engagement portion have a first inclined face and a second inclined face which engage each other, and the first inclined face and the second inclined face slidably contact each other while increasing or decreasing engaging force in proportion to a separated distance between the first and second holding assemblies according to driving of the second movement unit. Furthermore, the second movement unit may move the second holding assembly and the supporting member may support the first pressing unit. At this time, it is preferable that, when the second holding assembly is driven to move in a direction that the second holding assembly is separated from the first holding assembly, the first pressing unit moves along in a length direction of the tubes from a first pressing position where the second holding assembly is located before movement of the second holding assembly starts to a second pressing position while gradually increasing the pressing amount. Further, it is desirable that the first pressing unit which is located at the second pressing position presses the tubes with a pressing amount approximately equivalent to a pressing amount of the second pressing unit to the tubes.

Further, in the first aspect, the first holding assembly may be driven to move in a first direction which is a width direction of the tubes by the first movement unit, and the second holding assembly may be driven to move in a second direction which is a length direction of the tubes and which intersects the first direction by the second movement unit. At this time, it is preferable that the first movement unit moves the first holding assembly in the first direction to change relatively positions of the tubes cut by the cutting unit such that the end portions to be connected of the tubes face each other, the second movement unit moves the second holding assembly in the second direction such that the end portions to be connected of the tubes contact closely each other, and that a distance between the first pressing unit provided at the first holding assembly which is movable in the first direction and the cutting unit is set to be larger than a distance between the second pressing unit provided at the second holding unit which is movable in the second direction and the cutting unit, and it is more preferable that a moving distance of the first holding assembly in the first direction is set to be larger than a moving distance of the second holding assembly in the second direction.

Further, in order to achieve the above object, a second aspect of the present invention is directed to a tube connecting method for cutting and then connecting at least two flexible tubes, comprising the steps of: pressing the tubes put approximately in a parallel state at a first position on the tubes to deform the tubes to a flat state; pressing the tubes at a third position on the tubes which is adjacent to the first position to hold the tubes in a flat state; pressing the tubes at a second position on the tubes which is a position separate from the first position and which is a position opposing to the third position via the first position to hold the tubes in a flat state; advancing a cutting plate having a predetermined temperature between the second and the third positions to cut the tubes; moving relatively the tubes which have been cut to face one end portion and another end portion to be connected of the tubes; and evacuating the cutting plate from a predetermined cutting position located between the second and third positions to contact the end portions of the tubes closely each other for connecting the tubes.

In the second aspect, it is preferable that a pressing amount to the tubes is set to be gradually larger corresponding to a change in a pressing position on the tubes from the first position to the second position, and it is more preferable that a pressing amount to the first and second tubes at the second position is approximately equal to a pressing amount to the tubes at the third position.

BRIEF DESCRIPTION OF THE DRAWINGS

FIG. 8 is a perspective view showing operation for the main portions of the tube connecting apparatus in tube connecting process;

DETAILED DESCRIPTION OF THE PREFERRED EMBODIMENTS

With reference to the drawings, an embodiment of a tube connecting apparatus that cuts and then connects two tubes in which blood is contained and sealed and that the present invention is applied to will be explained below.

(Structure)

Figure 1:
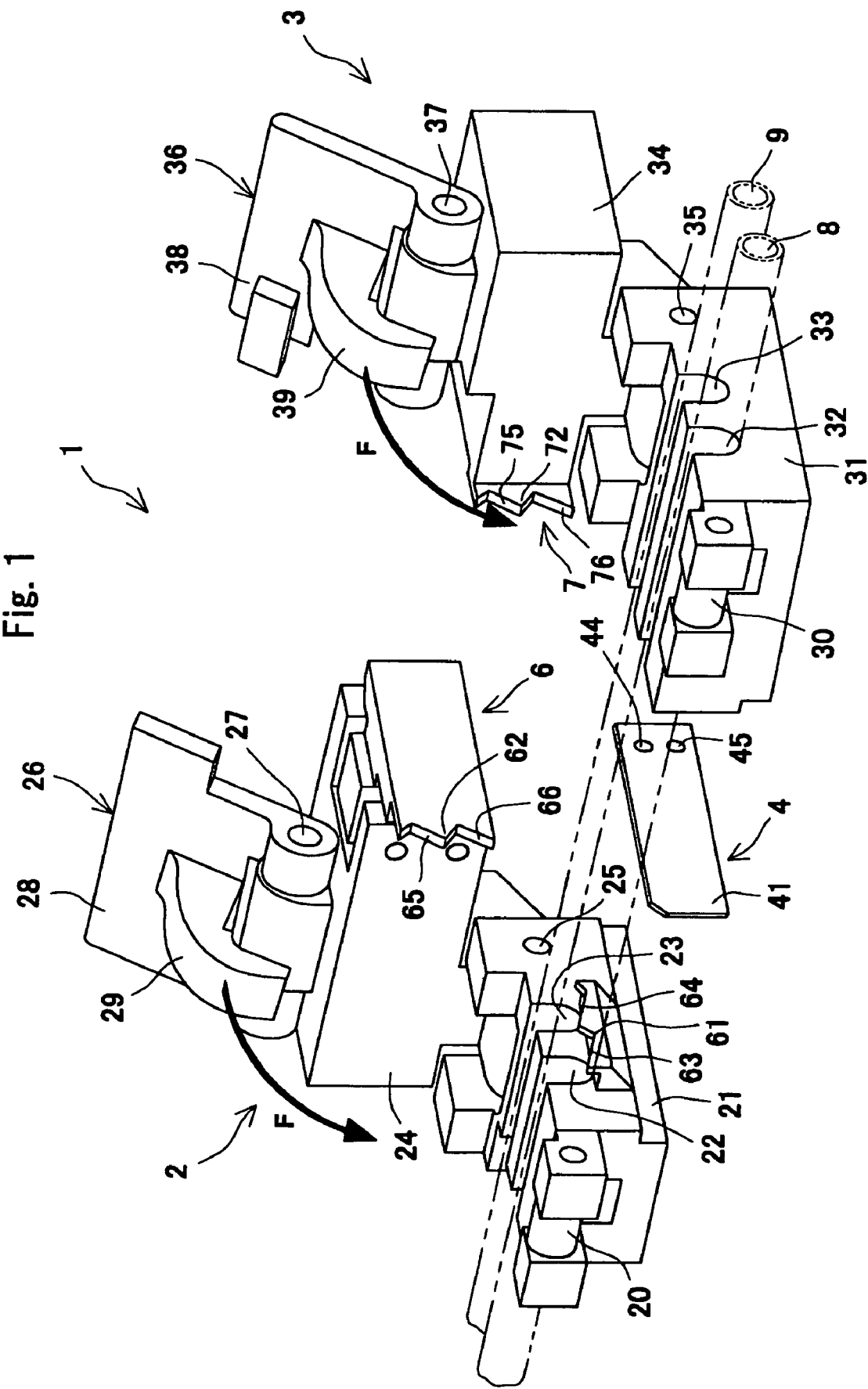
FIG. 1 is a perspective view showing main portions of a tube connecting apparatus of an embodiment to which the present invention is applicable.

As shown in FIG. 1, a tube connecting apparatus 1 of the present embodiment is equipped with a first tube-holding assembly 2 serving as a first holding assembly and a second tube-holding assembly 3 serving as a second holding assembly both of which hold two flexible tubes 8, 9 approximately in a parallel state, a cutting mechanism 4 which melts the tubes 8, 9 by heat for cutting the tubes and which serves as a cutting unit, a first clamp 6 serving as a first pressing unit and a second clamp 7 serving as a second pressing unit both of which press the tubes 8, 9 to a flat state.

The tubes 8, 9 are made of soft resin such as, for example, soft polyvinyl chloride or the like and have flexibility, in which blood is contained and sealed. These tubes 8, 9 have approximately the same shape with respect to an inner diameter, an outer diameter and a length in a state before blood is contained and sealed. (See FIG. 10A.) The first tube-holding assembly 2 has a holder 21 for holding the tubes 8, 9, and a covering body 24 which is fitted pivotably to a rear end portion of the holder 21 through a hinge 25 for opening and closing.

A pair of grooves 22, 23 which are parallel with each other and into which the two tubes 8, 9 are put (placed) are formed in the holder 21. A cross-section of the grooves 22, 23 is shaped as a letter U. It is preferable that a width of the grooves 22, 23 is set to have the same or a smaller width as/than a diameter of the tubes 8, 9 in an inartificial state. An operator pushes the tubes 8, 9 into inner sides thereof (downward direction) to put the tubes 8, 9 into the grooves 22, 23. The covering body 24, in a closed state, covers the grooves 22, 23 and has a function for fixing the tubes 8, 9 such that the tubes are put inside the grooves 22, 23 so as not to get rid of the grooves.

Further, the first tube-holding assembly 2 has a locking mechanism 26 for retaining the covering body 24 in a closed state. The locking mechanism 26 is constituted by a plate piece 28 which is fixed pivotably to a tip of the covering body 24 through a hinge 27, a pawl member 29 which is formed to protrude toward an inner face of the plate piece 28, and a stopping portion 20 which is formed at a front end of the holder 21. By pivoting the plate piece 28 in a direction of an arrow A in FIG. 1 to engage the pawl member 29 with the stopping portion 20 in a state that the covering body 24 is closed, the covering body 24 is locked so as not to open. For this reason, difficulties in cutting and connecting of the tubes are prevented since the covering body 24 is prevented from being opened unexpectedly during connecting of the tubes, and accordingly fixing (holding) to the tubes 8, 9 as well as pressing according to the first clamp 6 and the second clamp 7 stated later are not canceled.

The clamp 6 which presses the tubes 8, 9 to a flat state is provided (disposed) at the first tube-holding assembly 2 and at a side of the second tube-holding assembly 3. The first clamp 6 has a saw-shaped pressure closing member 61 which is fixed to a side face of the holder 21 and a saw-shaped pressure closing member 62 which is fixed to the covering body 24 so as to move in a vertical direction as stated later and which engages the pressure closing member 61. The pressure closing member 61 has inclined faces 63, 64 at positions corresponding to the grooves 22, 23 respectively, while inclined faces 65, 66, which are parallel to the inclined faces 63, 64 respectively and which are disposed at positions having a predetermined distance from the inclined faces 63, 64, are formed at the pressure closing member 62. Accordingly, when the covering body 24 is closed in a state that the tubes 8, 9 are put in the grooves 22, 23, the tube 8 is pressed by the inclined faces 63, 65 and the tube 9 is pressed by the inclined faces 64, 66 since the pressure closing members 61, 62 engage (bite) each other. The first clamp 6 restrains the tubes 8, 9 from dislocation (offset) or deformation and secures easy and proper connection when cut faces of the tubes 8, 9 are connected with each other, which will be stated later. Incidentally, the first clamp 6 is located in a state of contacting the second clamp 7 when the tubes 8, 9 are put in the grooves 22, 23 and the covering body 24 is set (for closing the covering body).

On the other hand, the second tube-holding assembly 3, in the same manner as the first tube-holding assembly 2, has a holder 31 at which a pair of grooves 32, 33 are formed and which holds the tubes 8, 9, a covering body 34 which pivots to the holder 31 for opening and closing, a locking mechanism 36 and the second clamp 7. A structure thereof corresponds to the first tube-holding assembly 2. The locking mechanism 36 has a hinge 37, a plate piece 38 and a pawl member 39, and the holder 31 has a hinge 35 and a stopping portion 30.

The second clamp 7 is constituted by a saw-shaped pressure closing member 71 (unillustrated) which is fixed to a side face of the holder 31 and at a side of the holder 21, and a saw-shaped pressure closing member 72 which is fixed to a side face of the covering body 34 and at a side of the covering body 24 and which bites the pressure closing member 71 each other. The pressure closing member 71 has inclined faces 73, 74 (unillustrated) at positions corresponding to the grooves 32, 33 respectively in the same manner as the pressure closing member 61. While, inclined faces 75, 76, which are parallel to the inclined faces 73, 74 respectively and which are disposed at positions having a predetermined distance from the inclined faces 73, 74, are formed at the pressure closing member 72.

The first tube-holding assembly 2 and the second tube-holding assembly 3 are usually located such that the grooves 22, 32 correspond to (align) the grooves 23, 33 respectively each other.

Figure 5A:
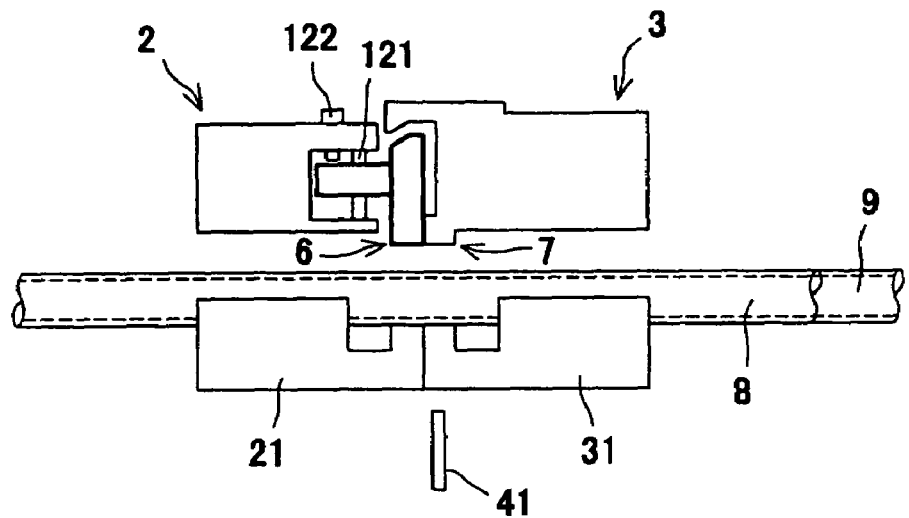
FIG. 5 is a front view showing operations for main portions of the tube connecting apparatus, FIG. 5A showing operation 1 thereof, FIG. 5B showing operation 2 thereof and FIG. 5C showing operation 3 thereof.

As shown in FIG. 5A, two shafts 121, which support the first clamp 6 such that the first clamp 6 is allowed to move in a separating/approaching direction to the tubes 8, 9 while slidably contacting the tubes 8, 9 and which serve as a supporting member, are set up in a traverse or width direction of the tubes 8, 9 put in the first tube-holding assembly 2. These shafts 121 penetrate unillustrated holes which are formed at the first clamp 6 and allow movement of the first clamp 6. Incidentally, a diameter of the unillustrated holes formed at the first clamp 6 is set to be slightly larger than that of the shafts 121 in order not only to restrain the first clamp 6 from dislocation or deformation in its movement but to give smooth movement to the first clamp 6.

The first clamp 6 supported by the shafts 121 maintains a state capable of free motion to the shafts 121 due to its self-weight, but when the first tube-holding assembly 2 having the first clamp 6 is set (for closing the covering body) to the tubes 8, 9, the first clamp 6 is forced to move upward after the tubes 8, 9 are pressed, and then, it is regulated so as to stop at a predetermined position.

They are adjusting screws 122 that regulate the position of the first clamp 6, which are fastened by thread adjacent to the shafts 121 at an upper portion of the first tube-holding assembly 2 and which serve as a position regulating member. (See FIG. 5A.) In the same manner as the shafts 121, two adjusting screws 122 are disposed in a traverse or width direction of the tubes 8, 9 put (held) in the first tube-holding assembly 2. (See FIG. 8.) By adjusting the adjusting screws 122 at predetermined positions in advance, the first clamp 6 can press the tube 8, 9 to a flat state with predetermined pressing force when the first tube-holding assembly 2 is set (for closing the covering body) to the tubes 8, 9.

Figure 5B:
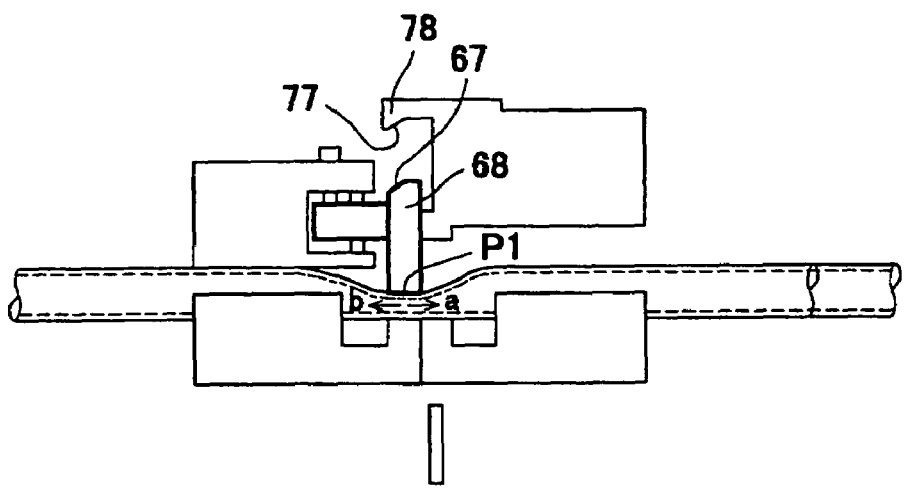

Further, as shown in FIG. 5B, an engagement portion 68 (a first engagement portion) having an inclined face 67 (a first inclined face) which is capable of engaging the second clamp 7 is formed at another end of the first clamp 6 to one end (a tip portion) at which the saw-shaped pressure closing member 62 is disposed. When the engagement portion 68 moves relative to an engagement portion 78 (a second engagement portion) having an inclined face 77 (a second inclined face) which is formed at the second clamp 7 in a state of sliding on the engagement portion 78, the engagement portion 68 functions to change a pressing amount (pushing amount) to the tubes 8, 9 gradually so as to displace a pressing position of the first clamp 6 to the tubes 8, 9.

Figure 4:
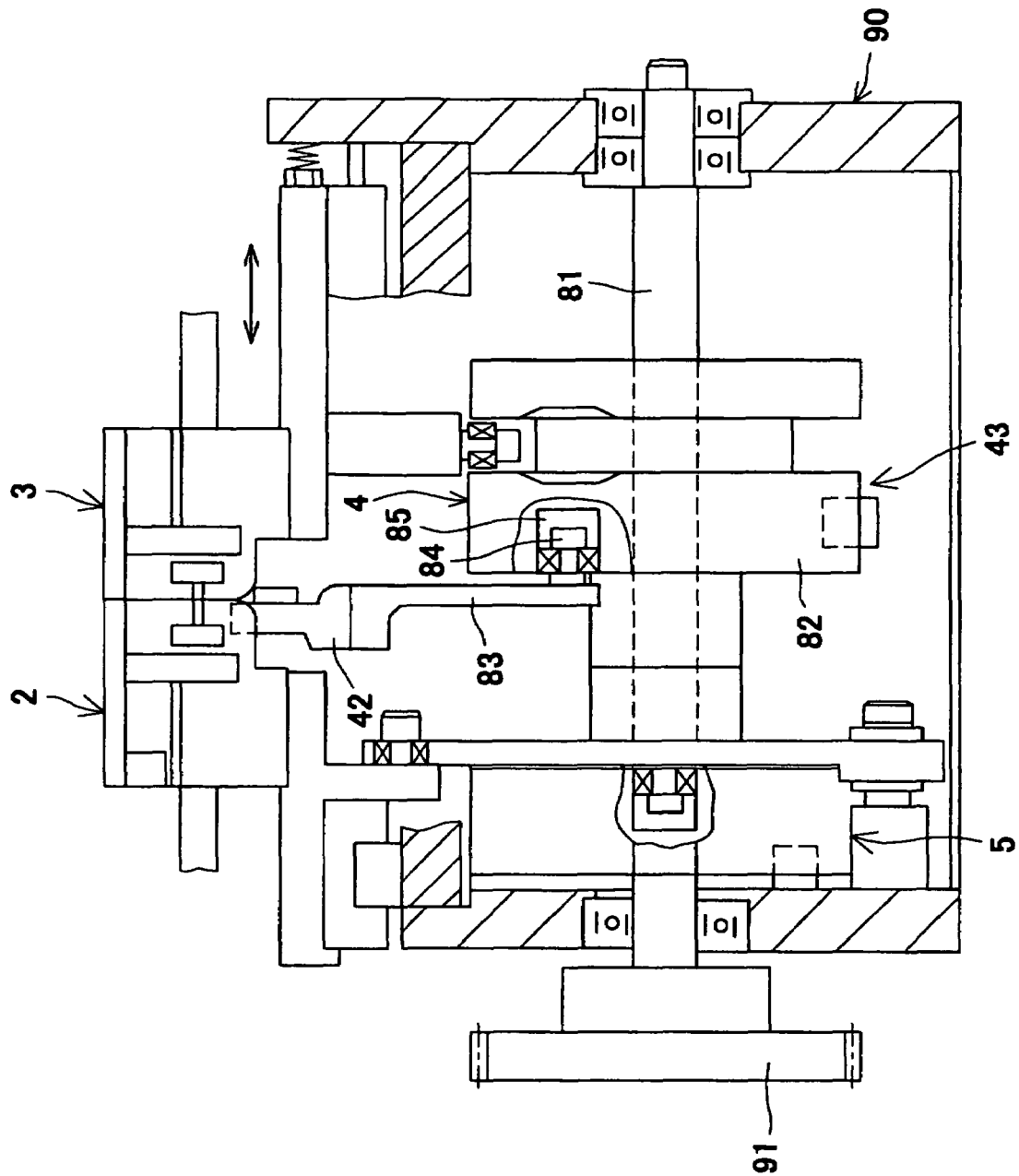
FIG. 4 is a partially broken plan view showing a first tube-holding assembly, a second tube-holding assembly and a cutting mechanism.

As shown in FIGS. 1 and 4, the cutting mechanism 4 is constituted by equipping a cutting plate (wafer) 41 for melting and cutting the tubes 8, 9, a holding member 42 which holds the cutting plate 41 in an exchangeable manner and at which an aperture is formed, and a cutting-plate movement mechanism 43 for moving the holding member 42 such that the cutting plate 41 inserts (advances) or evacuates (retreats) into/from a gap defined between the first tube-holding assembly 2 and the second tube-holding assembly 3.

The cutting plate 41 is a self-heating typed heat cutting plate, and a sheet of a metal plate such as a copper plate or the like is folded into two, a resistance body having a desired pattern for heating is formed inside the folded metal plate via insulating layers, and it has a structure that terminals 44, 45 disposed at both ends of the resistance body are exposed at apertures formed at each end portion of the metal plate.

When current is supplied between the terminals 44, 45 via an unillustrated current-carrying unit, the resistance body housed inside the cutting plate 41 generates heat and the cutting plate 41 is heated up to a temperature (ex. approximately 260 to 320 deg. C.) capable of melting and cutting the tubes 8, 9. Incidentally, it is preferable that the cutting plate 41 is disposable (for single use) at every connecting (joining) operation of the tubes. In this case, a structure may be employed that the cutting plate 41 to be held by the holding member 42 is replaced by a cutting-plate exchanging portion 46 (See FIGS. 2 and 3.) every time the tubes 8, 9 are connected.

The cutting-plate movement mechanism 43 is structured by equipping, as main parts, a cam 82 fitted to a rotation axis 81, an arm portion 83 extending downward the holding member 42, a following member 84 disposed at a tip of the arm portion 83 and extended to a side of the cam 82, fittings (unillustrated) to a main body 90, and an unillustrated hinge which supports the holding member 42 pivotably to the fittings. A cam groove 85 having a desired shape is formed at the cam 82 and the following member 84 is inserted into the cam groove 85 such that it can slide therein.

In accordance with rotation of the cam 82 according to rotation of the rotation axis 81, the following member 84 inserted into the cam groove 85 moves up and down, and the holding member 42 pivots around the unillustrated hinge. Accompanied by this movement, the holding member 42 rotates clockwise, and the cutting plate 41 in a heated state moves upward from an evacuated position and advances into the gap defined between the first tube-holding assembly 2 and the second tube-holding assembly 3, so that the tubes 8, 9 held by the grooves 22, 23 are melted and cut.

Figure 2:
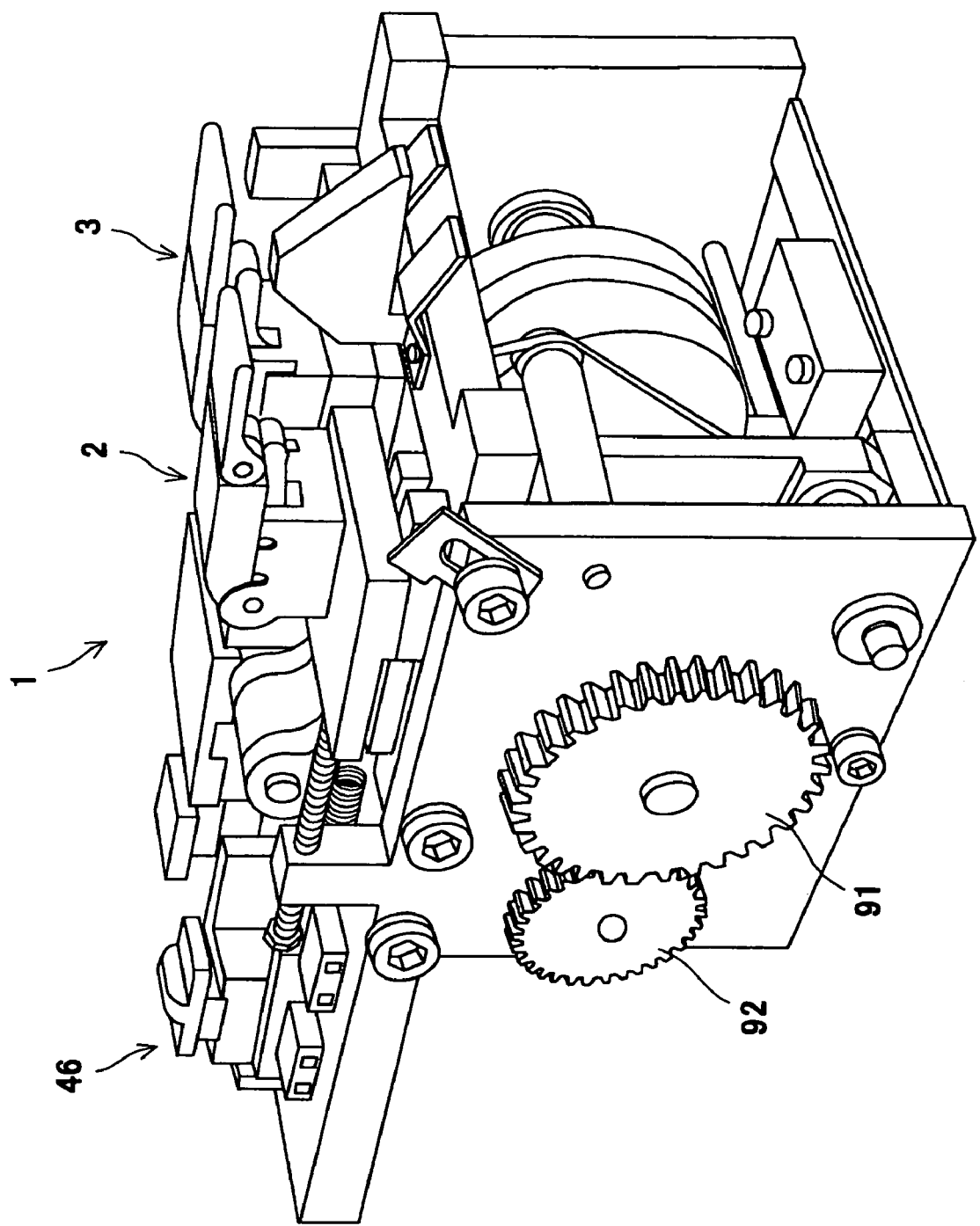
FIG. 2 is a schematic perspective view of the tube connecting apparatus in the embodiment.
Figure 3:
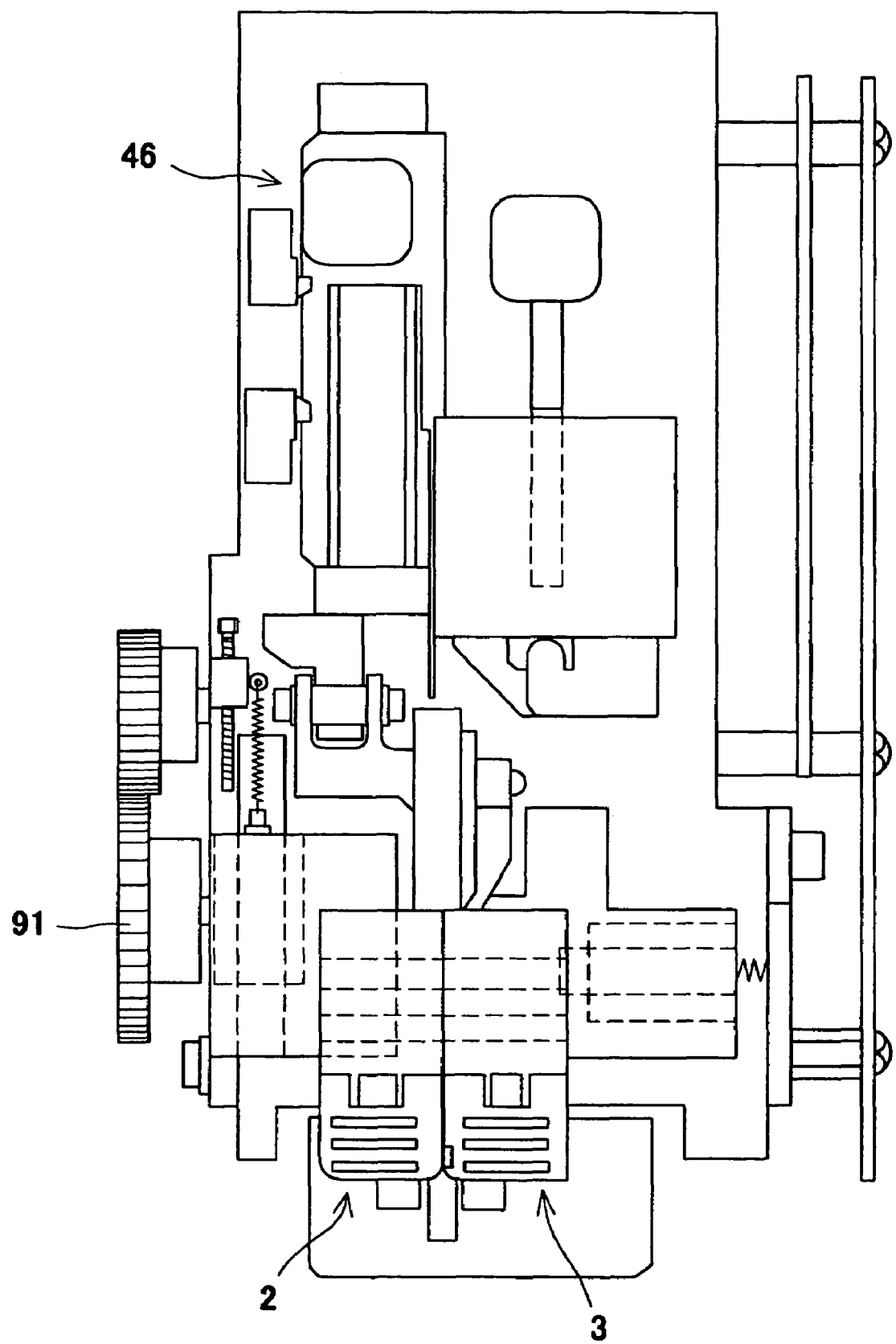
FIG. 3 is a plan view of the tube connecting apparatus.

Both ends of the rotation axis 81 are supported by bearings pivotably to the main body 90 and a gear 91 is fitted to one end portion of the rotation axis 81. As shown in FIG. 2, the gear 91 bites a small-diameter gear 92 fitted to a rotation axis of an unillustrated motor each other. When the motor is driven, rotation force thereof is conveyed via the small-diameter gear 92 and the gear 91 to the rotation axis 81 for rotation.

Further, the tube connecting apparatus 1 is equipped with movement mechanisms which move the first tube-holding assembly 2 and the second tube-holding assembly 3 respectively in a predetermined direction. The movement mechanisms are constituted by a first movement mechanism (unillustrated) which moves the first tube-holding assembly 2 to change positions of the tubes 8, 9 cut by the cutting mechanism 4 relatively such that end portions of the tubes to be connected face each other and which serves as a first movement unit, and a second movement mechanism (unillustrated) which moves the second tube-holding assembly 3 in a direction that the first clamp 6 and the second clamp 7 separate and in a direction that the end portions to be connected of the tubes 8, 9 cut by the cutting mechanism 4 contact closely each other. Such movement mechanisms can be structured, for example, by employing stepping motors, and the technique disclosed in the JPA 6-91010 or techniques of known liner stages or X-Y stages may be applicable.

Incidentally, the tube connecting apparatus 1 has a controlling unit structured with a CPU, a ROM, a RAM, an interface and the like at a downward position of the cutting-plate exchanging portion 46, and it is accommodated in an unillustrated casing such that the gear 91 and the small-diameter gear 92 are hidden.

(Operation)

Next, operation of the tube connecting apparatus 1 of the present embodiment will be explained.

First, an operator carries out operation for closing the covering body 24 of the first tube-holding assembly 2 and the covering body 34 of the second tube-holding assembly 3 to the tubes 8, 9 which are put in the grooves 22, 23, 32, and 33. (See FIG. 5A.) When the operator further continues to carry out the operation for closing the covering body 24, the pressure closing member 62 disposed at the tip portion of the first clamp 6 abuts and then deforms the tubes 8, 9, which are put in a parallel state at a first position P1 that is an abutting position, to a flat state. (See FIG. 5B.) At this time, blood inside the tubes 8, 9 at a portion which was pressed by the first clamp 6 is pushed out such that it is excluded in directions of an arrow a and an arrow b in FIG. 5B. Incidentally, the first clamp 6 is pushed back upward at the first position P1 due to reaction or repulsion force from the tubes 8, 9, and a part of the first clamp 6 abuts against lower ends of the above mentioned adjusting screws 122, thereby the first clamp 6 is regulated to stop at a predetermined position so as the first clamp 6 not to move in an upward direction which is a direction that the first clamp 6 further separates from the tubes 8, 9.

Figure 5C:
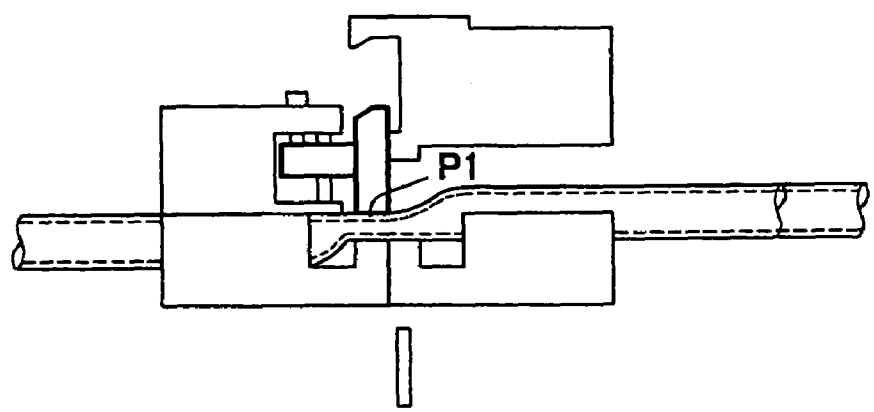

Subsequently, when the operation for closing the covering body 24 is carried out further, the pawl member 29 engages the stopping portion 20 of the locking mechanism 26 in the first tube-holding assembly 2, thereby the covering body 24 is locked so as not to open. In this state, the first clamp 6 deforms the tubes 8, 9 to a flat state at the first position P1 with predetermined pressing force. (See FIG. 5C.) The pressing force (pushing amount) of the first clamp 6 to the tubes 8, 9 at this moment can be adjusted optionally by the adjusting screws 122 depending on the material, the outer diameter size of the tubes and the like. However, it is preferable that the adjusting screws are adjusted to a degree that the tubes 8, 9 are not squashed too much.

Figure 6A:
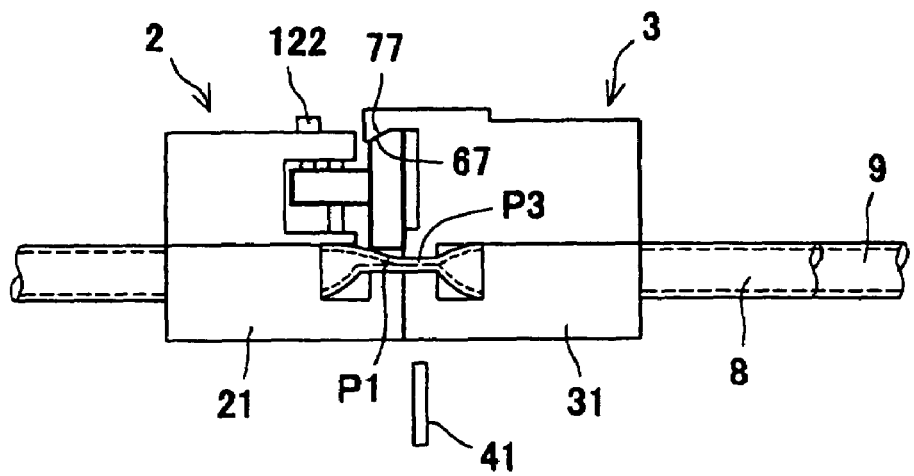
FIG. 6 is a front view showing operations for the main portions of the tube connecting apparatus, FIG. 6A showing operation 4 thereof, FIG. 6B showing operation 5 thereof and FIG. 6C showing operation 6 thereof.

Then, when the operation for closing the covering body 34 is carried out perfectly such that the pawl member 39 engages the stopping portion 30 at the locking mechanism 36 in the second tube-holding assembly 3 and the covering body 34 is locked so as not to open, the second clamp 7 which is located in a state of contacting the first clamp 6 presses and holds the tubes 8, 9 to a flat state in a state that the tubes are almost squashed (a state that blood inside the tubes hardly exists) at a third position P3 which is adjacent to the first position P1 with predetermined pressing force (which is larger than the pressing force due to the first clamp). (See FIG. 6A.) Thus, blood at the third position P3 corresponding to a portion pressed by the first clamp 7 is almost excluded in the tubes 8, 9. Pressing force (pushing amount) to the tubes 8, 9 by the first clamp 6 at the adjacent first position P1 is smaller than that by the second clamp 7 at the third position P3. In FIG. 6A, for its better understanding, a gap between the first clamp 6 and the tubes is illustrated, and a state that an interior of the tubes at a portion corresponding to a part of the first position P1 is widened is stressed. Further, at this time, the inclined face 67 of the first clamp 6 and the inclined face 77 of the second clamp 7 are located in a state of engaging each other as illustrated in FIG. 6A.

Fixing operation of the tubes 8, 9 is finished with the foregoing process, and process is shifted to squeezing operation for a portion of the tubes to be cut and tube-cutting process. When an operator pushes an unillustrated start button disposed at the tube connecting apparatus 1, the second tube-holding assembly 3 having the second clamp 7 which is in a state of contacting the first clamp 6 is driven to move in a direction that the first clamp 6 and the second clamp 7 separate (a direction of an arrow Y1 in FIG. 6B) by the above mentioned second movement mechanism (a state shown in FIG. 6B). This brings the inclined faces 67, 77 respectively disposed at the engagement portions 68, 78 for engaging each other in the first clamp 6 and the second clamp 7 to move relatively so as to slide in a contacting state at a predetermined angle of inclination. The first clamp 6, of which pressing force to the tubes 8, 9 is smaller than that of the second clamp 7, moves along a length direction of the tubes 8, 9 while gradually increasing its pressing force (pressing amount), then it is located at a second position P2 which is a position opposing to the third position P3 where the second clamp 7 presses and holds the tubes 8, 9 via the first position P1 to press and hold the tubes 8, 9 to a flat state. (See FIG. 6C.) In short, the first clamp 6 moves relatively to the tubes 8, 9 accompanied by squeezing operation or movement in a state that its pressing force (pressing amount) is gradually increased while slidably contacting the tubes 8, 9. The pressing force (pressing amount) of the first clamp 6 which is located at the second position P2 is set to be approximately equal to that of the second clamp 7 which presses and holds the tubes 8, 9 at the third position. In this state, blood inside the tubes 8, 9 from the second position P2 to the third position P3, namely, blood inside the tubes 8, 9 at portions being equivalent from a portion pressed by the first clamp 6 to a portion pressed by the second clamp 7 is almost excluded.

Pressing and holding operation of the tubes 8, 9 is finished with the foregoing process, and operation is shifted to the tube-cutting process.

Figure 7A:
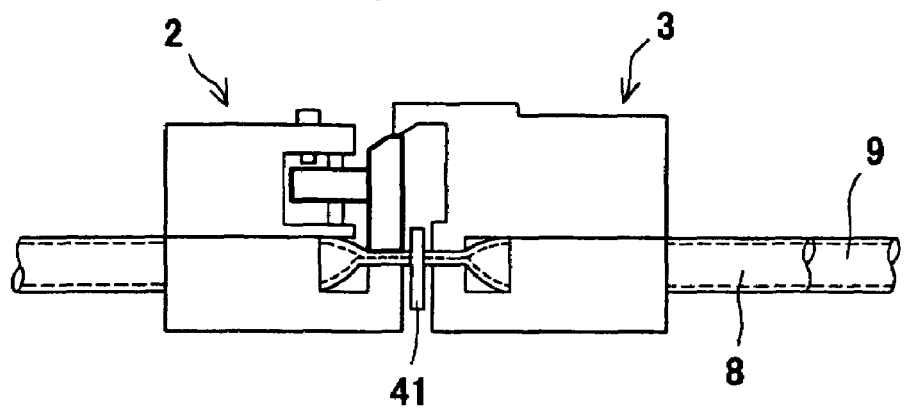
FIG. 7 is a front view showing operations for the main portions of the tube connecting apparatus, FIG. 7A showing operation 7 thereof, FIG. 7B showing operation 8 thereof and FIG. 7C showing operation 9 thereof.

Next, the cutting-plate movement mechanism 43 is activated at a predetermined timing and the heated cutting plate 41 ascends in accordance with ascending movement of the holding member 42. The cutting plate 41 continues its ascending movement and advances to a position between the second position P2 and the third position P3 to melt and cut the tubes 8, 9. (See FIG. 7A.)

Subsequently, the first tube-holding assembly 2 having the first clamp 6 is driven to move by a predetermined amount in a direction of an arrow X in FIG. 8 by the above mentioned first movement mechanism to move (change) positions of the cut tubes 8, 9 relatively such that the end portions to be connected of the tubes face each other. At this time, the cutting plate 41 which cut the tubes 8, 9 is retained at its cutting position in a stopped state.

Figure 6B:
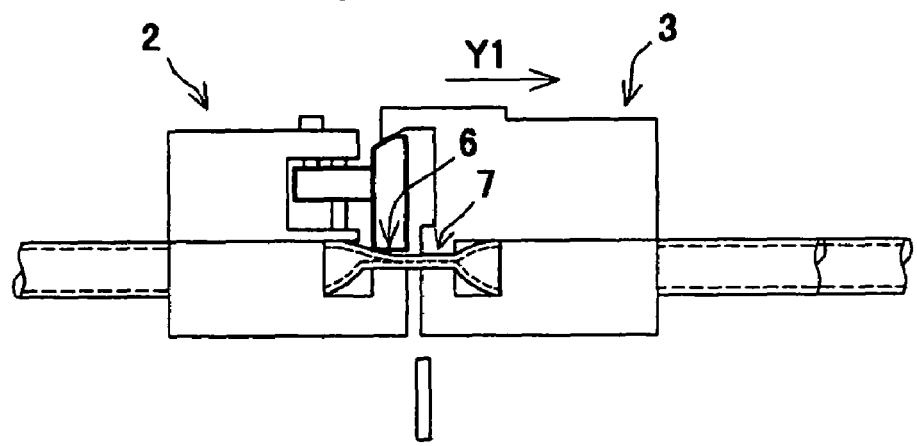
Figure 7B:
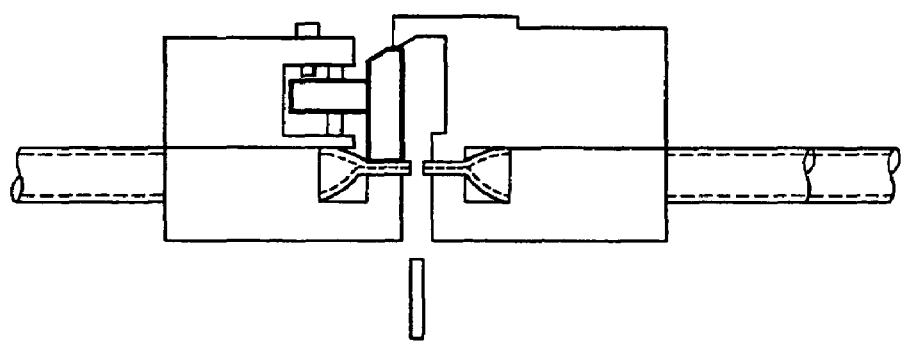

Thereafter, the cutting plate 41 descends to leave the cutting position (a state shown in FIG. 7B). Synchronizing with descending movement of this cutting plate 41, the second tube-holding assembly 3 having the second clamp 7 is driven to move by the second movement mechanism a predetermined amount in a direction of an arrow Y2 in FIG. 7C which is a direction approximately orthogonal to the arrow X in FIG. 8 and which is a direction opposite to the arrow Y1 shown in FIG. 6B. Thereby, the cut tubes 8, 9 move relatively and the facing ends of the tubes contact closely each other, and the tube connecting (process) is finished. (See FIG. 7C.) At this time, since the second tube-holding assembly 3 moves in the direction of the arrow Y2 in FIG. 7C, in place of the adjusting screws 122, stopping members capable of being moved by (an) actuator(s) may be employed in order to regulate the first clamp 6 from moving in the upward direction which is the direction that the first clamp 6 separates from the tubes 8, 9.

Moving amounts in the X and Y directions according to this embodiment will be explained in detail. The moving amount of the first tube-holding assembly 2 in the direction of the arrow X in FIG. 8 is set to 7.62 mm, the moving amount of the second tube-holding assembly 3 in the direction of the arrow Y1 in FIG. 6B is set to 0.9 mm, and the moving amount of second tube-holding assembly 3 in the direction of the arrow Y2 in FIG. 7 is set to 0.6 mm. 7.62 mm set for the moving amount of the first tube-holding assembly 2 is equivalent to a width length of the tubes 8, 9 which are put approximately in a parallel (row) state. With respect to the moving amounts in the Y direction, the test results for attaining the best connecting state were obtained by setting the separated distance between the assemblies to 0.9 mm at the time that the second tube-holding assembly 3 is located via the second clamp 7 to contact the first tube-holding assembly 2 having the first clamp 6 in an initial state before a series of the operations starts and then at the time of the operation for pressing and holding the tubes as shown in a state of FIG. 6C, by setting movement of the second tube-holding assembly 3 in the direction of the arrow Y2 in FIG. 7C to 0.6 mm at the time of connecting the tubes, and by setting the gap between the first clamp 6 and the second clamp 7 to 0.3 mm at the time of contacting the cut tubes 8, 9 closely each other.

Figure 9A:
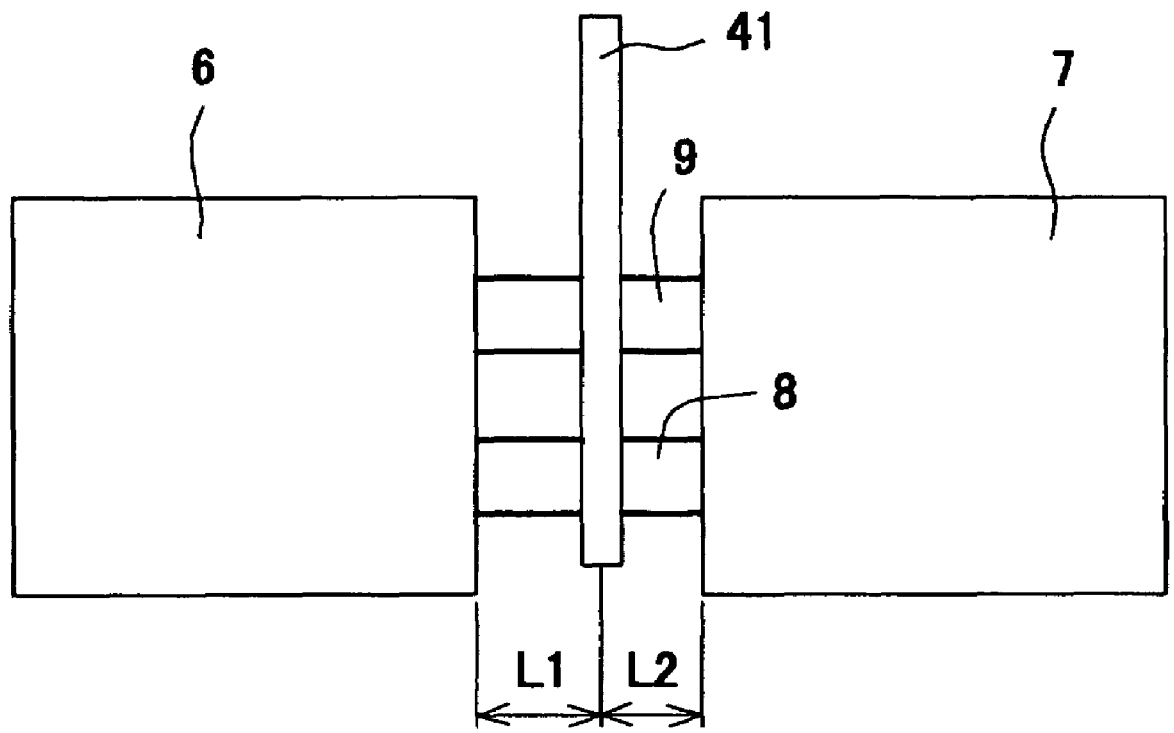
FIG. 9 is a plan view showing a first clamp, a second clamp and the cutting mechanism in the tube connecting process, FIG. 9A illustratively showing a relationship in a distance at a time of cutting the tubes, FIG. 9B illustratively showing side faces of a cutting plate when the tubes are moved in a direction of an arrow A in FIG. 8.

Further, as shown in FIG. 9A, in a state that the tubes 8, 9 are cut by the cutting plate 41, a distance L2 between the first clamp 7 and the cutting plate 41 is set to 0.17 mm while a distance L1 between the first clamp 6 and the cutting plate 41 is set to 0.45 mm. In short, the distance between the first clamp 6 and the cutting plate 41 is set to be larger than the distance between the second clamp 7 and the cutting plate 41. Incidentally, in FIG. 9A, both of the distances L1 and L2 are illustrated as distances from a position of a center line of the cutting plate 41 without taking a thickness of the cutting plate 41 into account.

Figure 10A:
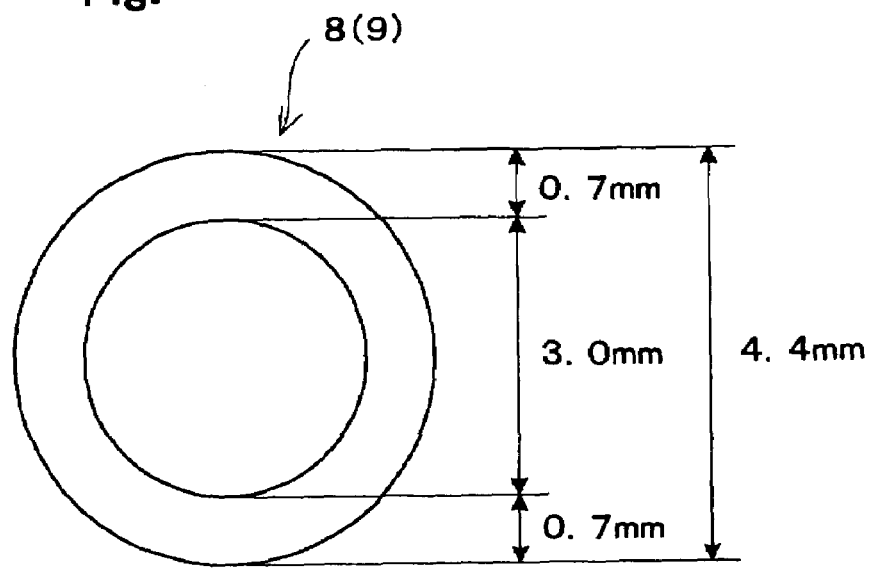
FIG. 10 is a sectional view of a tube used for the tube connecting apparatus of the embodiment, FIG. 10A showing an inartificial state of the tube, FIG. 10B showing a flat state when the tube is pressed, and FIG. 10C showing a flat state when the tube is further pressed.
Figure 10B:
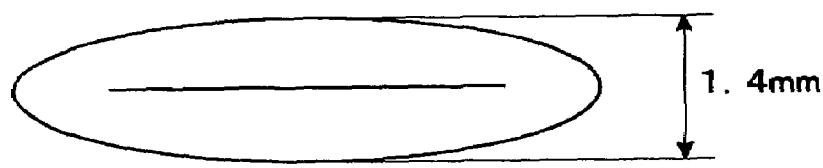

Next, the inartificial state of the tubes 8, 9 used for the tube connecting apparatus 1 and the flat state when the tubes are pressed will be explained further. As shown in FIG. 10A, in the inartificial state before being pressed to the flat states, the tubes 8, 9 are sized with an inner diameter of 3.0 mm and an outer diameter of 4.4 mm having a wall thickness of 0.7 mm in the state that blood is contained and sealed. In the above stated pressing and holding operation, when the tubes 8, 9 are pressed by the first clamp 6 at the first position P1, as shown in FIG. 10B, a portion of the inner diameter in which liquid is contained and sealed is pressed up to a degree that the tubes 8, 9 have a thickness of 1.4 mm such that each wall thickness of 0.7 mm is layered with each other in a vertical direction. Here, the pushing amount to the tubes is 3.0 mm which is equivalent to the above mentioned inner diameter according to calculation.

Figure 10C:
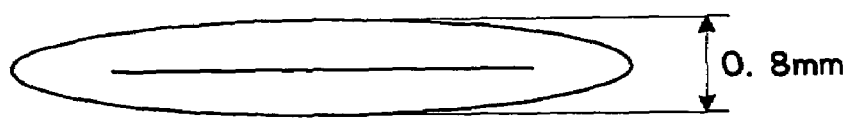

Further, when the second clamp 7 presses and holds the tubes 8, 9 at the third position P3 and when the first clamp 6 displaces the pressing position to press and hold the tubes at the second position P2, as a further pressed state, the tubes 8, 9 are pressed up to a thickness of 0.8 mm. (See FIG. 10C.) In other words, the pushing amount to the tubes at this time is 3.6 mm according to calculation.

As stated above, when displaced from the first position P1 to the second position P2, the first clamp 6 moves relatively to the tubes 8, 9 while increasing the pushing amount. The pushing amount to the tubes in this case further increases by 0.6 mm from 3.0 mm to 3.6 mm. The pushing amount of the first clamp 6 which is moved to the second position P2 to the tubes 8, 9 is equal (3.6 mm) to the pushing amount in the state that the second clamp 7 presses and holds the tubes 8, 9 at the third position P3.

(Effects and the Like)

Next, effects and the like of the tube connecting apparatus 1 in the present embodiment will be explained.

Figure 6C:
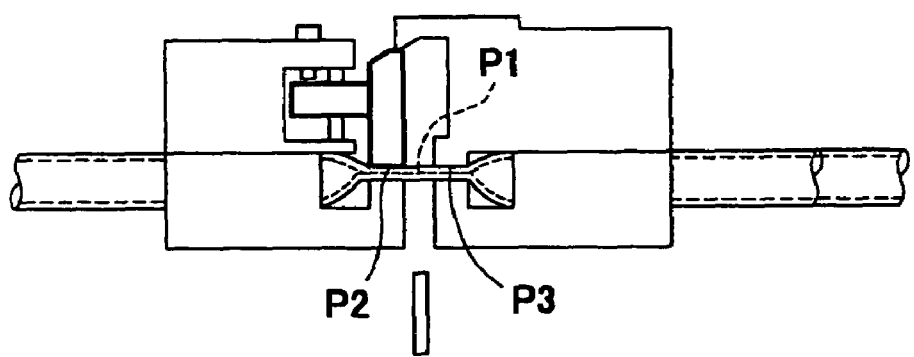
Figure 7C:
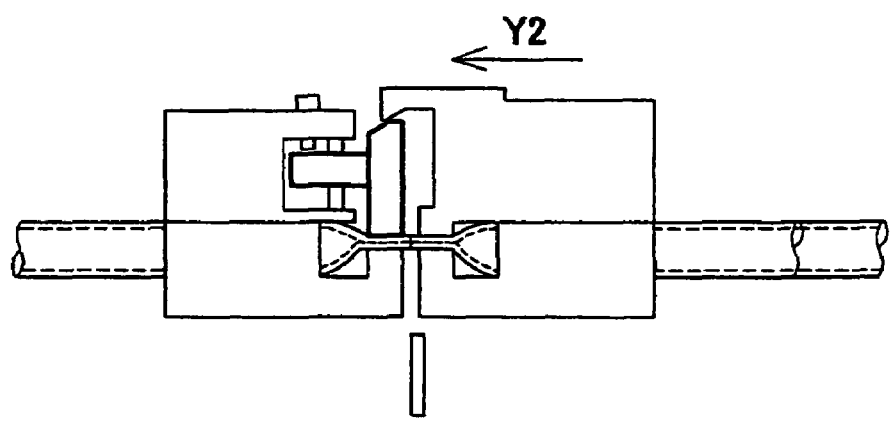

As stated above, in the tube connecting apparatus 1, the first clamp 6 and the second clamp 7 which press and hold the tubes 8, 9 are located (arranged) in a contact state, and when the second clamp 7 is driven to separate from the first clamp 6 by the second movement mechanism, the first clamp 6 moves from the first position P1 to the second position P2 while slidably contacting the tubes 8, 9 according to the shafts 121 which support the first clamp 6 so as the first clamp 6 to move vertically in a state of gradually increasing the pressing force to the tubes 8, 9 while squeezing the tubes 8, 9 due to sliding between the inclined faces 67 and 77 of the first engagement portion 68 and the second engagement portion 78 (FIGS. 6B and 6C). The pressing force to the tubes 8, 9 due to the squeezing operation can be adjusted to appropriate pressing force according to adjustment of the adjusting screws 121. Thus, residual blood from the third position P3 to the second position P2 via the first position P1 in the tubes 8, 9 is excluded or removed due to the squeezing operation carried out by the first clamp 6.

However, because a little blood remains at the end portions in the width direction of the tubes 8, 9 which were squashed to the flat state when the tubes 8, 9 were pressed (squashed) to exclude blood between the first clamp 6 and the second clamp 7, it was confirmed by tests that most of residual liquid existed at around a center portion between the first clamp 6 and the second clamp 7 in the length direction of the tubes 8, 9 when the cutting plate 41 advanced to cut the tubes 8, 9. If most of this residual liquid remains around the end portions to be connected, connecting strength (fusion strength) of the tubes drops. Particularly, in a case that the liquid inside the tubes 8, 9 is blood, since the connecting strength becomes weaker because blood components such as protein and the like remain there without vaporization, it is necessary to exclude the residual liquid existing around there.

Figure 9B:
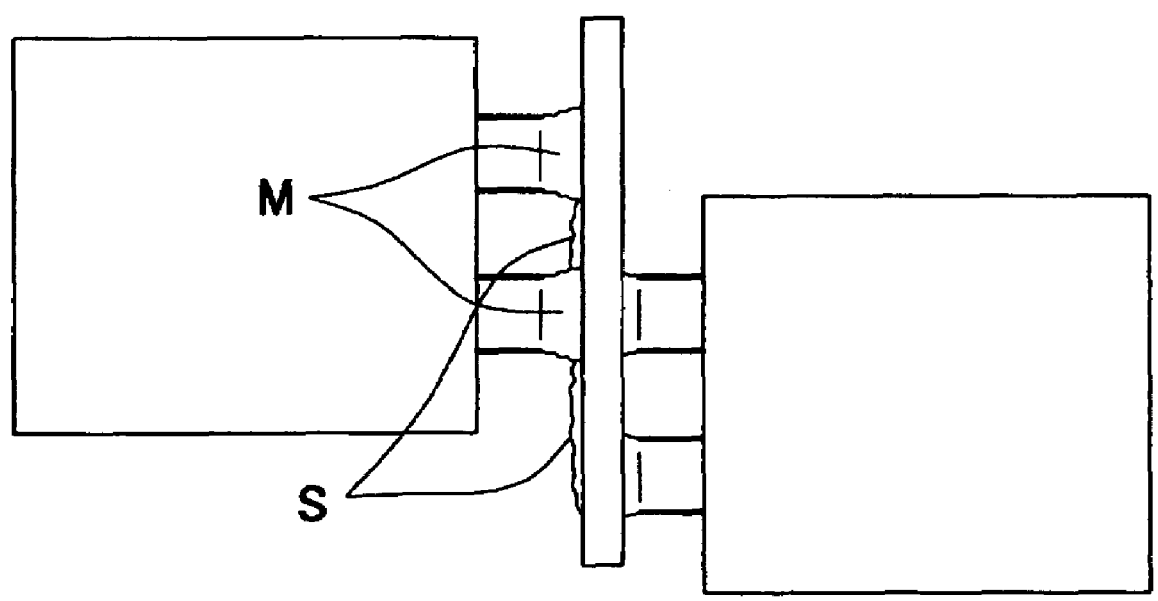

According to the tube connecting apparatus 1 of the present embodiment, when the first tube-holding assembly 2 having the first clamp 1 is driven to move by the predetermined amount in the direction of the arrow X in FIG. 8 by the first movement mechanism which moves the first tube-holding assembly 2 so as to move the positions of the cut tubes 8, 9 relatively to face the end portions of the tubes each other, the end portions of the tubes 8, 9 are moved so as to slidably contact the heated cutting plate 41. Under a concept that a part around the end portions is melt further by heat, the distances among the first clamp 6, the second clamp 7 and the cutting plate 41 are set such that the distance between the first clamp 6 provided at the first tube-holding assembly 2 which moves the end portions to be connected of the tubes so as to face each other and the cutting plate 41 is set to be larger than that of another. Thus, the tube connecting apparatus 1 can realize stable and reliable tube connecting by further melting thermally around the center portion of the tubes (portion of reference M in FIG. 9B) where the residual blood exists to exclude the residual liquid at the time of moving the tubes. It should be noted that blood components such as protein and the like in the excluded residual liquid adhere to the side faces of the cutting plate 41 with which the tubes contacted at the time of moving the tubes as shown in FIG. 9B. (See reference S in FIG. 9B.) Therefore, according to the tube connecting apparatus 1 of the present embodiment, a large effect that the tubes in which blood is contained and sealed are connected stably and reliably can be obtained. However, the tube connecting apparatus 1 is not limited to the same. It can also realize stable tube connecting in use either in a case of connecting between a tube in which blood is contained and an empty tube or in a case of connecting between empty tubes in which blood is not contained; both have been carried out conventionally.

Further, the tube connecting apparatus 1 of the present embodiment can realize wet-to-wet connecting between the tubes easily and rapidly under a sterilized condition only by putting the tubes 8, 9 in which blood is contained and sealed into the grooves 22, 23, 32 and 33 and locking the covering bodies 24, 34 with the locking mechanisms 26, 36. Because such a tube connecting apparatus has been requested to realize from a public view, an industrial value thereof seems to be extremely high.

Incidentally, in the present embodiment, the tube connecting apparatus which connects the two tubes in which blood is contained and sealed was shown. However, the present invention is not restricted to the same. It is also applicable to a tube connecting apparatus which connects three tubes or more, or a tube connecting apparatus which connects tubes in which liquid other than blood is contained and sealed properly each other.

Further, in the present embodiment, an example that the second tube connecting assembly 3 having the second clamp 7 is moved when the first clamp 6 and the second clamp 7 separate was shown. However, the first tube-assembly 2 having the first clamp 6 may be moved, or, both may be moved at the same time. In other words, even in any structure for moving the assembly or assemblies, since the pressing position of the second clamp 7 side having the larger pressing amount to the tubes 8, 9 is unchanged and accordingly the first clamp 6 having the smaller pressing amount can not maintain the holding (clamping) state to the tubes 8, 9, the first clamp 6 necessarily displaces the position while slidably contacting the tubes 8, 9.

Furthermore, in the present embodiment, an example that the first movement mechanism and the second movement mechanism, which constitute the movement mechanisms, move the assemblies respectively in one direction of the X direction or Y direction (and opposite direction thereto) was shown. However, the present invention is not confined to the same. A tube connecting apparatus may be structured in a manner that the mechanisms move the assemblies two-dimensionally or three-dimensionally. Such a structure enables sooner tube connecting.

Moreover, in the present embodiment, the saw-shaped pressure closing members 61, 62, 71 and 72 were explained. However, since it is sufficient for these members to have a function for pushing out and excluding blood in the tubes 8, 9, they may press and close the tubes 8, 9, for example, at their horizontal faces, or they may have a structure that inclination at a side of the second clamp 7 is formed to protrude a little with respect to the inclined faces 65 and 66 of the pressure closing member 62, which slidably contacts the tubes 8, 9, of the first clamp 6 so as to exclude residual liquid easily when the first clamp 6 moves relatively to the tubes 8, 9 from the first position P1 to the second position P2. Further, the cutting plate 41 is not limited to the self-heating typed one. For example, the plate may have a structure heated by a heat source such as an electric heater.

What is claimed is:

1. A tube connecting apparatus having a first holding assembly and a second holding assembly which hold at least two flexible tubes approximately in a parallel state, comprising:
   a first pressing unit which is provided at the first holding assembly and which presses the tubes to a flat state;
   a second pressing unit which is provided at the second holding assembly and which presses the tubes to a flat state and which is allowed to be located so as to contact the first pressing unit;
   a supporting member which supports at least one of the first and second pressing units such that a pressing amount of the at least one of the first and second pressing units to the tubes changes;
   a cutting unit which cuts the tubes between the first and second pressing units;
   a first movement unit which moves at least one of the first and second holding assemblies to change relatively positions of the tubes cut by the cutting unit such that end portions to be connected face each other; and
   a second movement unit which moves at least one of the first and second holding assemblies in a direction that the first pressing unit and the second pressing unit separate and a direction that the end portions to be connected of the tubes cut by the cutting unit contact closely each other,
   wherein the first pressing unit has a first engagement portion and the second pressing unit has a second engagement portion,
   wherein the first engagement portion and the second engagement portion have a first inclined face and a second inclined face respectively which engage each other,
   and wherein, when at least one of the first and second holding assemblies is driven to move in a direction that the holding assemblies separate from each other by the second movement unit, the supporting member gradually changes the pressing amount of the at least one of the first and second pressing units to the tubes by the first inclined face and the second inclined face slidably contacting each other while increasing or decreasing engaging force.

2. A tube connecting apparatus according to claim 1, further comprising a position regulating member which regulates at a predetermined position the at least one of the first and second pressing units supported by the supporting member.

3. A tube connecting apparatus according to claim 1, when the at least one of the first and second holding assemblies is driven to move in a direction that the holding assemblies separate from each other by the second movement unit, the supporting member gradually increases the pressing amount of the at least one of the first and second pressing units to the tubes in accordance with a moving amount of the supporting member by the first inclined face and the second inclined face slidably contacting each other while increasing engaging force.

4. A tube connecting apparatus according to claim 1, wherein the second movement unit moves the second holding assembly and the supporting member supports the first pressing unit.

5. A tube connecting apparatus according to claim 4, wherein, when the second holding assembly is driven to move in a direction that the second holding assembly is separated from the first holding assembly by the second movement unit, the first pressing unit moves along a length direction of the tubes from a first pressing position where the second holding assembly is located before movement of the second holding assembly starts to a second pressing position while gradually increasing the pressing amount.

6. A tube connecting apparatus according to claim 5, wherein the first pressing unit which is located at the second pressing position presses the tubes with a pressing amount approximately equivalent to a pressing amount of the second pressing unit to the tubes.

7. A tube connecting apparatus according to claim 1, wherein the first holding assembly is driven to move in a first direction which is a width direction of the tubes by the first movement unit, and the second holding assembly is driven to move in a second direction which is a length direction of the tubes and which intersects the first direction by the second movement unit.

8. A tube connecting apparatus according to claim 7, wherein the first movement unit moves the first holding assembly in the first direction to change relatively positions of the tubes cut by the cutting unit such that the end portions to be connected of the tubes face each other, the second movement unit moves the second holding assembly in the second direction such that the end portions to be connected of the tubes contact closely each other, and wherein a distance between the first pressing unit provided at the first holding assembly which is movable in the first direction and the cutting unit is set to be larger than a distance between the second pressing unit provided at the second holding unit which is movable in the second direction and the cutting unit.

9. A tube connecting apparatus according to claim 8, wherein a moving distance of the first holding assembly in the first direction is set to be larger than a moving distance of the second holding assembly in the second direction.

10. A tube connecting method for cutting and then connecting at least two flexible tubes, comprising the steps of:

pressing the tubes put approximately in a parallel state at a first position on the tubes to deform the tubes to a flat state;

pressing the tubes at a third position on the tubes which is adjacent to the first position to hold the tubes in a flat state;

pressing the tubes at a second position on the tubes which is a position separate from the first position and which is a position opposing to the third position via the first position to hold the tubes in a flat state;

advancing a cutting plate having a predetermined temperature between the second and the third positions to cut the tubes;

moving relatively the tubes which have been cut to face one end portion and another end portion to be connected of the tubes; and evacuating the cutting plate from a predetermined cutting position located between the second and third positions to contact the end portions of the tubes closely each other for connecting the tubes, wherein, when Dressing the tubes at the second position, a pressing position on the tubes is changed from the first position to the second position and a pressing amount to the tubes is set to be gradually larger corresponding to the change in the pressing position on the tubes.

11. A tube connecting method according to claim 10, wherein a pressing amount to the first and second tubes at the second position is approximately equal to a pressing amount to the tubes at the third position.

* * * * *